United States Patent [19]

Suzuki et al.

[11] 4,015,591

[45] Apr. 5, 1977

[54] CHOLESTERIC LIQUID CRYSTALLINE PHASE MATERIAL-DYE COMPOSITION AND VENAPUNCTURE METHOD EMPLOYING THE COMPOSITION

[75] Inventors: Fred K. Suzuki, Arlington Heights; Thomas W. Davison, Streamwood, both of Ill.

[73] Assignee: Liquid Crystal Products, Inc., Arlington Heights, Ill.

[22] Filed: Feb. 17, 1976

[21] Appl. No.: 658,407

[52] U.S. Cl. .............................. 128/2 R; 128/2 H; 23/230 LC; 73/356; 252/408

[51] Int. Cl.² ........................................ A61B 10/00

[58] Field of Search ........... 128/2 F, 2 G, 2 H, 2 R, 128/399, DIG. 5; 73/356; 252/408 LC; 23/230 LC

[56] References Cited

UNITED STATES PATENTS

| | | | |
|---|---|---|---|
| 2,544,659 | 3/1951 | Dreyer | 23/230 LC |
| 2,746,264 | 5/1956 | Keyes | 128/399 |
| 3,433,216 | 3/1969 | Mattson | 128/2 F |
| 3,533,399 | 10/1970 | Goldberg et al. | 73/356 |
| 3,576,761 | 4/1971 | Davis | 23/230 LC |
| 3,765,243 | 10/1973 | Pickett et al. | 73/356 |
| 3,766,061 | 10/1973 | Mahler et al. | 252/408 LC |
| 3,782,365 | 1/1974 | Pinna | 128/2 R |
| 3,920,574 | 11/1975 | Brown, Jr. et al. | 23/230 LC |

Primary Examiner—William E. Kamm
Attorney, Agent, or Firm—John S. O'Brien

[57] ABSTRACT

A composition of matter having thermal color responsive characteristics and adapted for exhibiting improved color contrast includes an enantiotropic cholesteric liquid crystalline phase material, and at least two oil-soluble dyes dissolved in the material in a total dye concentration of 0.01–1% by weight of the composition, each of the dyes reflecting light of a different wave length in the range of 400 to 700 nanometers, and said dyes together absorbing light of substantially all wave lengths within said range. A method of effecting venapuncture in the human body includes the steps of cooling the skin over a venous area, applying directly on the skin a layer of the composition about 100 to 300 microns thick, allowing the skin over the venous area to rewarm due to venous blood flow, until the said material exhibits a mesophase color change to thereby delineate a vein therebeneath, and directing an instrument for venapuncture to a site in the said area indicated by the delineation to constitute the location of a vein.

20 Claims, No Drawings

CHOLESTERIC LIQUID CRYSTALLINE PHASE MATERIAL-DYE COMPOSITION AND VENAPUNCTURE METHOD EMPLOYING THE COMPOSITION

BACKGROUND OF THE INVENTION

This invention relates to compositions containing cholesteric liquid crystalline phase materials and their utilization. More particularly, the invention relates to a composition of a cholesteric liquid crystalline phase material and oil-soluble dyes, and to a venapuncture method employing the composition for vein location.

Cholesteric liquid crystalline phase materials, also referred to as cholesteric liquid crystals, their technology and applications are reviewed in the book by Peter L. Carroll entitled "Cholesteric Liquid Crystals", June, 1973 (Ovum Ltd., London). The materials, hereinafter referred to for convenience simply as "liquid crystals", are a class of compounds that display a cholesteric mesophase within certain temperature limits. When liquid crystals are in such phase, and ordinary white light is directed at the material, the light is separated essentially into two components, one of which is transmitted and one of which is scattered or reflected. The scattered light gives the material an irridescent color, which depends upon the material, the temperature, and the angle of the incident light beam. The cholesteric mesophase is a state of matter intermediate in molecular ordering between a crystalline solid and an isotropic liquid. In general, the materials are colorless in their solid and isotropic liquid states, assuming the coloration of their background or of light-absorptive materials added thereto.

Prior patents relating to thermal color responsive or temperature sensitive cholesteric liquid crystal compositions and their use in applications where temperature is to be measured or a temperature pattern is to be observed include U.S. Pat. Nos. 3,114,836, 3,441,513 and 3,533,399, the latter patent having to do with the production of visible patterns corresponding to skin temperature patterns in human beings. Reports on the application of liquid crystal thermography to examination of the body include an article by Davison, Ewing, Fergason, Chapman, Can, and Voorhis, "Detection of Breast Cancer by Liquid Crystal Thermography", *Cancer*, Vo. 29, No. 5, page 1123, May, 1972, and an article by Davison, Ewing, Sayat, Mulla, and Fergason, "Liquid Crystal Thermographic Placental Location", *Obstetrics and Gynecology*, Vol. 42, No. 4, page 574, October, 1973.

In order to improve color contrast, the liquid crystals commonly are applied to and viewed against an absorptive, particularly a black background, which serves to absorb the transmitted light. Alternatively, absorptive, generally black particulate material is admixed with the liquid crystals, so as to absorb the transmitted light while not interfering excessively with the intensity of the scattered light. As an additional alternative, it has been proposed to incorporate black or colored dyes in the liquid crystal compositions. The incorporation of dyes is disclosed in the above-identified book by Carroll, particularly, pages 102 and 197, the patents identified therein, i.e., U.S. Pat. Nos. 3,647,279 and 3,666,947 and West German Pat. No. 2,012,493, and also U.S. Pat. Nos. 3,627,699 and 3,656,909.

Liquid crystal compositions in which black pigments or oil-soluble black dyes are incorporated provide the black background needed for observing liquid crystal coloration. However, color intensity is diminished with their use, so that they are added in proportions such as to balance the desired colored contrast with the color intensity. As a result, neither contrast nor intensity reaches a desired level for certain applications. While colored dyes have been incorporated in liquid crystal compositions, as disclosed in the patents and publication identified above, it appears that they have been used principally to accomplish other objectives, such as to absorb ultraviolet or infrared radiation.

The most common technique for applying liquid crystals to measure or map temperatures, as on a surface of the body, is to first blacken the surface with an aqueous, oil-impervious black paint, then apply liquid crystals from a solution by brushing or spraying. This procedure is time-consuming, and cannot be used when instant observation of temperatures or thermal gradients is required. Liquid crystals dispersed in films and having a black backing or black filler for absorbing transmitted light have been applied to surfaces, including body skin, for measuring temperatures and for thermal mapping. The use of films for rapid temperature measurement and thermal mapping has been limited owing to their inability to conform to surface contours.

There has long been a need for a rapid method of greater reliability for locating veins in the human body, in hospitals, clinics and laboratories, preparatory to drawing blood or making intravenous injections or infusions. While body vascular patterns have been mapped by liquid crystal thermography, as reported in the references identified above, the prior techniques have not been applied to the problem of effecting venapuncture in the human body, apparently due to the limitations thereof which prevent such an operation from being effected rapidly and/or reliably.

SUMMARY OF THE INVENTION

The invention provides a composition of matter having thermal color responsive characteristics and adapted for exhibiting improved color contrast, and when employed in a layer of suitable thickness, exhibiting high color intensity, which composition is especially advantageous for effecting venapuncture according to the invention, and is also useful in other applications. The invention also provides a method of effecting venapuncture in the human body, employing the new composition, which fills the need for a rapid and reliable technique, especially for locating the deeper and more difficult to locate subcutaneous veins.

More particularly, a composition of matter according to the invention includes an enantiotropic cholesteric liquid crystalline phase material, and at least two oil-soluble dyes dissolved in the material in a total dye concentration of 0.01–1% by weight of the composition, each of the dyes reflecting light of a different wave length in the range of 400 to 700 nanometers, and the dyes together absorbing light of substantially all wave lengths within the range. A layer of the new composition having a thickness of about 100 to 300 microns exhibits both improved color contrast and high color intensity.

The composition may be applied to a body surface and the results may be observed rapidly, in a matter of seconds, in a very simple procedure. The composition displays brilliant colors with good contrast, so that venapuncture may follow immediately. Similarly, the composition may be employed for evaluation of peripheral vascular conditions of the hands, arms, feet, legs and face, and to evaluate inflammatory conditions of the body. The composition also has commercial and industrial applications, where temperature indication or thermal mapping is desirable.

The method of effecting venapuncture according to the invention includes the steps of (a) in any order, (1) cooling the skin over a venous area of the body, and (2) applying directly on the skin over said area a layer about 100 to 300 microns thick of the new composition, the cholesteric liquid crystalline phase material of such composition exhibiting a mesophase color change at a temperature reached by the skin upon rewarming due to venous blood flow; (b) allowing the skin over the area to rewarm due to venous blood flow, until said material exhibits a mesophase color change to thereby delineate a vein therebeneath; and (c) directing an instrument for venapuncture to a site in the venous area indicated by the foregoing delineation to constitute the location of a vein.

The new method may be performed with a high degree of accuracy, which is especially important in directing an instrument to a relatively deep vein. The method is also highly compatible with the necessity for rapid venapuncture in hospitals, clinics and laboratories.

DESCRIPTION OF THE PREFERRED EMBODIMENTS

Enantiotropic cholesteric liquid crystalline phase materials or liquid crystals which may be employed in the invention are well-known and readily may be selected for intended uses following the teachings of the prior art, including the patents and publications cited above. Thus, for example, liquid crystals which may be employed are described in detail in U.S. Pat. Nos. 3,114,836, 3,441,513, and 3,533,399. Most commonly, two, three or four-component liquid crystal compositions are employed, for providing a desired color response, and a mesophase or color-play temperature range at a desired temperature level and having a suitable width of temperature range. Preferably, the liquid crystals are selected to provide a color response in the mesophase range changing with increasing temperature from red through orange, yellow, green, and blue to violet in the visible spectrum, as a result of light scattering by the liquid crystals. Reference to an "enantiotropic" material means a liquid crystal which forms, or a mixture of liquid crystals which together form the cholesteric mesophase either by heating the material in its crystalline solid phase or by cooling the material in its isotropic liquid phase.

Preferred liquid crystals include the cholesteryl, dicholesteryl, cholestanyl, and sitosteryl organic esters, halides or alkyl carbonates. Table 1 is a list of liquid crystals which are further preferred in the invention.

Table 1

| | |
|---|---|
| Cholesteryl erucyl carbonate | (CEC) |
| Cholesteryl methyl carbonate | (CMC) |
| Cholesteryl oleyl carbonate | (COC) |
| Cholesteryl para-nonyl phenyl carbonate | (CNPC) |
| Cholesteryl phenyl carbonate | (CPC) |
| Cholesteryl acetate | (CA) |
| Cholesteryl benzoate | (CBz) |
| Cholesteryl butyrate | (CB) |
| Cholesteryl isobutyrate | (CiB) |
| Cholesteryl chloride | (CCl) |
| Cholesteryl chloroacetate | (CCA) |
| Cholesteryl cinnamate | (CCn) |
| Cholesteryl crotanoate | (CCr) |
| Cholesteryl decanoate | (CDc) |
| Cholesteryl erucate | (CE) |
| Cholesteryl heptanoate | (CHp) |
| Cholesteryl hexanoate | (CHx) |
| Cholesteryl laurate | (CLa) |
| Cholesteryl myristate | (CMy) |
| Cholesteryl nonanoate | (CN) |
| Cholesteryl octanoate | (COt) |
| Cholesteryl oleate | (CO) |
| Cholesteryl propionate | (CP) |
| Cholesteryl valerate | (CV) |
| Dicholesteryl carbonate | (DCC) |
| Cholestanyl Benzoate | (CaBz) |
| Sitosteryl nonanoate | (SN) |

Preferred liquid crystal compositions and their mesophase temperature ranges are listed in Table 2.

Table 2

| Comp. No. | Components of Composition in % by weight | | | | Mesophase Temperature Range, °C |
|---|---|---|---|---|---|
| 1. | 52%CN | 32%COC | 7%CBz | 9%DCC | 31 – 34 |
| 2. | 60%CN | 25%COC | 15%CBz | | 30 – 37 |
| 3. | 56%CN | 35%COC | 9%CBz | | 32 – 35 |
| 4. | 75%CN | 9%COC | 16%CP | | 29 – 37 |
| 5. | 75%CN | 10%COC | 15%CA | | 30 – 38 |
| 6. | 78%CN | 5%COC | 17%CP | | 34 – 37 |
| 7. | 85%CN | 5%COC | 10%CV | | 30 – 36 |
| 8. | 50%CN | 26%COC | 14%CBz | 10%CNPC | 29 – 33 |
| 9. | 50%CN | 33%COC | 8%CBz | 9%DCC | 28 – 33 |
| 10. | 56%CN | 44%COC | | | 31 – 32 |
| 11. | 48%CN | 44%COC | 8%DCC | | 31 – 33 |
| 12. | 47%CN | 43%COC | 7%DCC | 3%CCl | 30 – 33 |
| 13. | 23%CN | 60%CO | 17%CCr | | 29 – 31 |
| 14. | 70%CEC | 15%CCr | 15%CPC | | 28 – 30 |
| 15. | 40%CN | 40%CO | 5%CCr | 15%CaBz | 30 – 34 |
| 16. | 5%CN | 80%CO | 6%CCr | 15%CaBz | 33 – 36 |
| 17. | 80%CN | 20%CiB | | | 61 – 67 |
| 18. | 61%CN | 28%CiB | 11%CB | | 40 – 60 |
| 19. | 63%CN | 16%CiB | 16%CB | | 30 – 50 |
| 20. | 80%COC | 20%CHx | | | 8 – 12 |
| 21. | 71%COC | 24%CHx | 5%CBz | | 0 – 8 |
| 22. | 67%COC | 23%CHx | 10%CC | | −20 to −3 |

Composition numbers 1 through 16 are useful for application to the human body, including vein location and evaluation of vascular and inflammatory conditions. Composition numbers 17 through 19 are useful for industrial, non-destructive testing. Composition numbers 20 through 22 are useful, inter alia, for leak detection in refrigeration.

Body skin temperatures in general may range from 30 to 37° C in venous areas, and may go down to 25° C or up to 39° C. The skin temperature varies over the surface of the body. For example, it may vary 6° C around the circumference of the arm at the elbow, with the atmosphere at room temperature. It is preferred that compositions for application to the body have a mesophase temperature range in the range of 25°–40° C, more preferably, 28°–38° C, as illustrated by composition numbers 1–16. The width of the mesophase temperature range preferably is from about 1° C to about 7° C in venapuncture applications. Greater color differentiation is obtained between areas of differing temperatures as the width of the temperature range increases, and temperature sensitivity increases with decreasing width of the range.

The liquid crystal composition for venapuncture use is selected to exhibit a mesophase color change at a temperature reached by the skin upon rewarming due to venous blood flow. Preferably, but not necessarily, the normal skin temperature above the vein falls within the mesophase temperature range. Liquid crystal compositions having a mesophase temperature range of 30°–37° C are advantageous for widespread application. In the majority of cases, a mesophase temperature range of about 31°–34° C for the composition appears to be optimum. Compositions having other temperature ranges may be employed to accommodate various skin temperatures which may be encountered in connection with venapuncture applications. Other applications of the composition to examination of the body may render it preferable to employ various ones of composition numbers 1–16 and others.

Dyes are selected so that each reflects light of a different wave length in the visible spectrum, i.e., 400 to 700 nanometers. That is, each of the dyes reflects a different one of the colors present in ordinary white light, reference to color herein being exclusive of black. The dyes are selected so that together, they absorb light of substantially all wave lengths within the foregoing range, and they are blended for most brilliant color intensity of the liquid crystals. It has been found that excellent results are obtained when the individual dye colors and concentrations are selected to produce a dye mixture having a violet, brown, or brown-black color at room temperature.

The combination or mixture of dyes is incorporated in a composition with the liquid crystals in a total dye concentration of 0.01–1% by weight of the composition, preferably, in a concentration of about 0.05–0.3%. The dye combination incorporated in such a proportion serves to absorb light of the visible spectrum that is transmitted, or not scattered by the liquid crystals upon irradiation with white light. At the same time, the dye combination absorbs scattered light to a markedly lesser degree than when employing an otherwise adequate amount of a black dye or pigment. Consequently, the iridescent colors of selectively scattered light are observed with markedly improved color contrast.

Table 3 is a list of oil-soluble dyes which may be employed in the invention, the dyes dissolving in liquid crystals and providing the desired absorbance.

Table 3

| Dyes Identified By Color Index & Generic Name | Chemical Type | Color-Hue |
| --- | --- | --- |
| C.I. Solvent Yellow 5 | Monoazo | Reddish Yellow-Orange |
| C.I. Solvent Yellow 33 D & C Yellow II | Quinoline | Greenish-Yellow |

Table 3-continued

| Dyes Identified By Color Index & Generic Name | Chemical Type | Color-Hue |
| --- | --- | --- |
| C.I. Solvent Yellow 30 | Diazo | Yellow |
| C.I. Solvent Orange 2 D & C Orange 2 | Monoazo | Reddish Orange |
| C.I. Solvent Orange 17 D & C Orange 14 | Xanthene | Orange |
| C.I. Solvent Red 23 D & C Red 17 | Diazo | Yellow Red-Red |
| C.I. Solvent Red 27 D & C Red 18 | Diazo | Bluish Red |
| C.I. Solvent Red 49 D & C Red 37 | Xanthene | Bluish Pink |
| C.I. Solvent Green 3 D & C Green 6 | Anthraquinone | Bluish Green |
| C.I. Solvent Green 7 D & C Green 8 | Anthraquinone | Yellowish Green |
| C.I. Solvent Violet 13 D & C Violet 2 | Anthraquinone | Bluish Violet |
| C.I. Solvent Violet 17 | | Violet |

Table 4 is a list of preferred dye combinations or mixtures for addition to liquid crystals. Composition numbers 1 and 2 in Table 4 are further preferred.

Table 4

| Dye Mixtures, in % by wt. of Composition | Color of Combination at Room Temperature |
| --- | --- |
| 1. 0.1% C.I. Solvent Violet 13<br>0.02–0.05% C.I. Solvent Yellow 33<br>0.02–0.05% C.I. Solvent Red 23 | Deep Violet |
| 2. 0.05% C.I. Solvent Violet 13<br>0.05% C.I. Solvent Yellow 33<br>0.05% C.I. Solvent Red 49 | Brown |
| 3. 0.1% C.I. Solvent Violet 17<br>0.1% C.I. Solvent Green 7 | Brown |
| 4. 0.1% C.I. Solvent Violet 13<br>0.1% C.I. Solvent Red 49<br>0.1% C.I. Solvent Yellow 5 | Brown-Black |
| 5. 0.2% C.I. Solvent Violet 13<br>0.1% C.I. Solvent Orange 2 | Violet |
| 6. 0.1% C.I. Solvent Violet 17<br>0.05% C.I. Solvent Yellow 5<br>0.05% C.I. Solvent Green 3 | Brown |

The new composition of liquid crystals and dyes is employed in a layer having a thickness of about 100 to 300 microns, thereby providing high color intensity as well as improved color contrast. While the invention is not limited to theoretical considerations, it appears that the improved color contrast results both from the presence of the dyes and from the layer thickness, and the high color intensity results from the layer thickness and the low dye concentration. Liquid crystal application thickness affects scattered light intensity and spatial resolution, the intensity increasing and the resolution decreasing with increasing layer thickness. The invention takes advantage of the fact that to achieve its objects, particularly vein location, high spatial resolution is not essential, whereby a relatively thick layer may be employed and serves to provide excellent color intensity and improved color contrast. The low dye concentration employed not only minimizes effect on scattered light intensity, but avoids deleterious action on the liquid crystals by the dyes acting as impurities.

Inasmuch as organic solvents for the liquid crystals alter the optical effects, and in view of the difficulty in removing all traces of solvent, particularly in layer thicknesses of the above magnitude, it is preferred that the new composition be provided in the form of an organic solvent-free paste. Such a paste may be packaged in and dispensed from a tube, or from a pressurized container or other container adapted to dispense metered amounts or slugs of the paste, for example. The paste may be dispensed from a container under the pressure of a highly volatile solvent, such as one of the Freons, for example, which will evaporate very rapidly and not affect the optical properties of the liquid crystals. The paste may be spread on a surface in the desired thickness, using a spatula, with a finger of the hand, or in another suitable manner.

In proceeding according to the method of the invention for effecting venapuncture or venasection in the human body, the skin over a venous area is cooled. The cooling may take place before, during or after application of the composition containing liquid crystals. The purpose of the cooling is to produce a greater temperature gradient between the skin surface directly over a vein and adjacent areas of the skin, to thereby provide a sharper delineation of the vein. Cooling removes the heat supplied to the skin by various physiological sources, and thereafter, rewarming takes place most rapidly over the veins, due to the blood flow therein.

The cooling procedure, per se, is known, being described in the above-identified publications of Davison et al, among others. Various methods of cooling may be employed, including application of cooled liquids, evaporative cooling by applying liquids of low boiling point, cooling by application of cold air or inert gas, cooling by the propellant such as a Freon employed for applying a liquid crystal paste, or a combination of such methods. Cooling may be combined with cleansing of the skin prior to venapuncture.

As examples of coolants that may be employed, the skin may be cooled with refrigerated liquids such as water, one to three-carbon alcohols, and aqueous one to three-carbon alcohols. Evaporative cooling may be effected with diethyl ether, five to six-carbon alkanes, acetone, fluorocarbons such as the Freons boiling above 25° C, and petroleum ether (30°–60° C boiling range). Preferred are mixtures of diethyl ether-acetone, hexane-acetone, ethanol or isopropanol-acetone or diethyl ether, each in a volume ratio from about 1:4 to 4:1, preferably about 1:1, petroleum ether (30°–60° C), and the foregoing fluorocarbons.

It is preferred that the skin be cooled to a temperature below the mesophase temperature range for the liquid crystal composition and, generally, that the skin be cooled to a temperature in the range of about 25°–28° C. However, and particularly with a relatively wide mesophase temperature range, it is not essential that the skin be cooled completely below the mesophase range, although it must be cooled below the upper limit of such range to provide the color differentiation necessary for accurate venapuncture.

The composition containing liquid crystals is applied directly on the skin over the venous area, in a layer about 100 to 300 microns thick, as described above. The composition is spread transversely across an arm, for example, in a layer preferably about 1 centimeter wide. An indication of a vein appears, in a period of time from substantially instantaneously up to about 20 seconds, and averaging about 3–5 seconds, depending upon the temperatures involved and physiological factors.

The venous area is the most rapidly rewarming area, and is indicated by the first color to appear, where cooling to below the mesophase temperature range was achieved, and in any event, by the shortest wave length color present. As the skin continues to warm, the color of the venous area goes through the above-described color changes from red to violet, to the extent that the skin reaches a temperature corresponding to a particular color of the liquid crystals. The specific appearance of the venous area will vary under varying circumstances, and it may appear as a line, an ellipitcal area, or a spot. At this time, if desired, the skin may be marked in some manner to indicate the location of the vein, either in the area covered with the composition, or adjacent thereto where a needle or other instrument is to be inserted. For example, a temporary indentation may be made in the skin with a blunt instrument.

A tourniquet is applied in the usual manner prior to venapuncture, to increase the pressure of the returning blood and distend the vein. In view of the rapidity of the entire operation, the tourniquet may be applied at any time, preferably prior to application of the composition.

A needle for venapuncture is inserted ordinarily about one-half centimeter below the area having the composition thereon, and the needle is angled beneath the skin in the direction of the coated area, to puncture the vein, in the usual manner. Alternatively, after marking the skin to indicate vein location, the composition may be removed prior to insertion of the needle, with a cotton swab containing a solvent, such as ethanol-ether or aqueous isopropanol. The entire process is completed in a relatively short period of time by a competent technician.

The following examples illustrate the manner in which compositions may be prepared and venapuncture may be effected in accordance with the invention. It will be understood that the invention is not limited to the materials, proportions, conditions and procedures employed in the examples, which are merely illustrative. The proportions in the examples are by weight.

EXAMPLE 1

A 100-gram quantity of liquid crystal composition number 1 of Table 2 is formulated in a Pyrex beaker and heated to melting temperature on a hot plate with gentle stirring, employing a magnetic stirring bar. The mixture becomes a single phase liquid upon heating for one minute at 60° C.

A mixture of dyes is dissolved in the molten liquid crystal at 60° C, the mixture containing the following dyes in the proportions indicated:

| Component | Proportion, Grams |
|---|---|
| C.I. Solvent Violet 13 | 0.10 |
| C.I. Solvent Yellow 33 | 0.05 |
| C.I. Solvent Red 23 | 0.05 |

The resulting composition may be packaged in five 1-ounce ointment tubes, in 20-gram aliquots. The tubes are cooled at room temperature to 25°–30° C, and the tubes are crimped to seal them. Each tube can be used for 40–60 vein locations.

In one manner of effecting venapuncture, an area for vein location is selected in the forearm, adjacent to the elbow, and the area is cleansed and cooled with a copious quantity of refrigerated (10° C) isopropanol rubbing alcohol. About 0.3 to 0.5 gram of the composition is applied to the clean area, and the composition is smoothed over a four inch square area using the finger of one hand. Color usually appears within several seconds. The warmest temperatures, corresponding to vein locations, are indicated by the first appearance of red color and, thereafter, by the color of the shortest wave length, which most frequently appears as elliptical lines over superficial veins.

A vein location in the covered area may be marked by a slight depression in the skin, made with a blunt object. The composition then may be removed from the skin by wiping with cotton soaked in aqueous isopropanol or ethanol-diethyl ether. A tourniquet is applied to the arm at any time prior to venapuncture. A needle is directed to a site in the arm beneath the depression in the skin, being inserted in the skin at a location spaced below or laterally from the depression made in the arm, and then being angled upwardly or in a direction towards the depression, for puncturing the vein with the needle at an acute angle thereto. Alternatively, the needle may be inserted while the composition remains to indicate the vein location, in which case, the insertion is made at a location spaced below or laterally from the area covered with the composition.

EXAMPLE 2

A 100-gram quantity of liquid crystal composition number 2 of Table 2 is compounded with dye mixture number 2 of Table 4, following the procedure of Example 1. The resulting composition may be employed in effecting venapuncture, in the same manner as with the composition of Example 1.

While certain preferred embodiments of the invention have been described, it will be apparent to those skilled in the art that various changes and modifications may be made therein within the spirit and scope of the invention. It is intended that such changes and modifications be included within the scope of the appended claims.

We claim:

1. A composition of matter having thermal color responsive characteristics and adapted for exhibiting improved color contrast which comprises an enantiotropic cholesteric liquid crystalline phase material, and at least two oil-soluble dyes dissolved in said material in a total dye concentration of 0.01–1% by weight of the composition, each of said dyes reflecting light of a different wave length in the range of 400 to 700 nanometers, and said dyes together absorbing light of substantially all wave lengths within said range.

2. A composition as defined in claim 1 wherein said dyes together exhibit a violet, brown, or brown-black color at room temperature.

3. A composition as defined in claim 2 wherein said dyes are selected from the group consisting of dyes having the Color Index designations: Solvent Yellow 5, Solvent Yellow 30, Solvent Yellow 33, Solvent Orange 2, Solvent Orange 17, Solvent Red 23, Solvent Red 27, Solvent Red 49, Solvent Green 3, Solvent Green 7, Solvent Violet 13, and Solvent Violet 17.

4. A composition as defined in claim 3 wherein said material is selected from the group consisting of cholesteryl, dicholesteryl, cholestanyl, and sitosteryl organic esters, halides, and alkyl carbonates.

5. A composition as defined in claim 4 in the form of an organic solvent-free paste.

6. A composition as defined in claim 5 wherein said dyes comprise a mixture of about 0.1% C.I. Solvent Violet 13, 0.02–0.05% C.I. Solvent Yellow 33, and 0.02–0.05% C.I. Solvent Red 23, in percentages by weight of said composition.

7. A layer of the composition of claim 6 having a thickness of about 100 to 300 microns, said layer exhibiting improved color contrast and high color intensity.

8. A composition as defined in claim 1 having a mesophase temperature range in the range of 25°–40° C.

9. A composition as defined in claim 1 wherein said material is selected from the group consisting of cholesteryl, dicholesteryl, cholestanyl, and sitosteryl organic esters, halides, and alkyl carbonates.

10. A composition as defined in claim 1 in the form of an organic solvent-free paste.

11. A layer of the composition of claim 1 having a thickness of about 100 to 300 microns, said layer exhibiting improved color contrast and high color intensity.

12. A method of effecting vanapuncture in the human body which comprises:
   a. in any order, (1) cooling the skin over a venous area of the body, and (2) applying directly on the skin over said area a layer about 100 to 300 microns thick of a composition having thermal color responsive characteristics, said layer exhibiting improved color contrast and high color intensity, said composition comprising an enantiotropic cholesteric liquid crystalline phase material exhibiting a mesophase color change at a temperature reached by the skin upon rewarming due to venous blood flow, and at least two oil-soluble dyes dissolved in said material in a total dye concentration of 0.01–1% by weight of the composition, each of said dyes reflecting light of a different wave length in the range of 400 to 700 nanometers, and said dyes together absorbing light of substantially all wave lengths within said range;
   b. allowing the skin over said area to rewarm due to venous blood flow, until said material exhibits a mesophase color change to thereby delineate a vein therebeneath; and
   c. directing an instrument for venapuncture to a site in said area indicated by said delineation to constitute the location of a vein.

13. A method as defined in claim 12 wherein the mesophase temperature range of said material falls within the range of 25°–40° C, and the skin temperature following said cooling is below said mesophase temperature range.

14. A method as defined in claim 12 wherein the mesophase temperature range of said material is about 31°–34° C, and the skin temperature following said cooling is about 25°–28° C.

15. A method as defined in claim 12 wherein said dyes together exhibit a violet, brown, or brown-black color at room temperature.

16. A method as defined in claim 12 wherein said material is selected from the group consisting of cholesteryl, dicholesteryl, cholestanyl, and sitosteryl organic esters, halides, and alkyl carbonates.

17. A method as defined in claim 12 wherein said dyes are selected from the group consisting of dyes having the Color Index designations: Solvent Yellow 5, Solvent Yellow 30, Solvent Yellow 33, Solvent Orange 2, Solvent Orange 17, Solvent Red 23, Solvent Red 27, Solvent Red 49, Solvent Green 3, Solvent Green 7, Solvent Violet 13, and Solvent Violet 17.

18. A method of effecting venapuncture in the human body which comprises:

a. in any order, (1) cooling the skin over a venous area of the body, and (2) applying directly on the skin over said area a layer about 100 to 300 microns thick of a composition having thermal color responsive characteristics and being in the form of an organic solvent-free paste, said layer exhibiting improved color contrast and high color intensity, said composition comprising an enantiotropic cholesteric liquid crystalline phase material having a mesophase temperature range within the range of 28°–38° C and exhibiting a mesophase color change at a temperature reached by the skin upon rewarming due to venous blood flow, the skin temperature following said cooling being below said mesophase temperature range, and at least two oil-soluble dyes dissolved in said material in a total dye concentration of 0.01–1% by weight of the composition, each of said dyes reflecting light of a different wave length in the range of 400 to 700 nanometers and being selected from the group consisting of dyes having the Color Index designations: Solvent Yellow 5, Solvent Yellow 30, Solvent Yellow 33, Solvent Orange 2, Solvent Orange 17, Solvent Red 23, Solvent Red 27, Solvent Red 49, Solvent Green 3, Solvent Green 7, Solvent Violet 13, and Solvent Violet 17, and said dyes together absorbing light of substantially all wave lengths within said range and exhibiting a violet, brown, or brown-black color at room temperature;

b. allowing the skin over said area to rewarm due to venous blood flow, until said material exhibits a mesophase color change to thereby delineate a vein therebeneath; and c. directing an instrument for venapuncture to a site in said area indicated by said delineation to constitute the location of a vein.

19. A method as defined in claim 18 wherein said material is selected from the group consisting of cholesteryl, dicholesteryl, cholestanyl, and sitosteryl organic esters, halides, and alkyl carbonates.

20. A method as defined in claim 19 wherein said dyes comprise a mixture of about 0.1% C.I. Solvent Violet 13, 0.02–0.05% C.I. Solvent Yellow 33, and 0.02–0.05% C.I. Solvent Red 23, in percentages by weight of said composition.

* * * * *